(12) United States Patent
Choshi et al.

(10) Patent No.: US 7,327,861 B2
(45) Date of Patent: Feb. 5, 2008

(54) ORGANISM AUTHENTICATING APPARATUS

(75) Inventors: Kinya Choshi, Osaka (JP); Yusuke Kaneda, Osaka (JP)

(73) Assignee: Bionics Co., Ltd., Osaka (JP)

( * ) Notice: Subject to any disclaimer, the term of this patent is extended or adjusted under 35 U.S.C. 154(b) by 733 days.

(21) Appl. No.: 10/467,348

(22) PCT Filed: Feb. 25, 2002

(86) PCT No.: PCT/JP02/01635

§ 371 (c)(1),
(2), (4) Date: Aug. 20, 2003

(87) PCT Pub. No.: WO02/069260

PCT Pub. Date: Sep. 6, 2002

(65) Prior Publication Data

US 2004/0071322 A1    Apr. 15, 2004

(30) Foreign Application Priority Data

Feb. 26, 2001  (JP)  ............................. 2001-049823
Jul. 5, 2001   (JP)  ............................. 2001-204314

(51) Int. Cl.
*G06K 9/00*  (2006.01)
(52) U.S. Cl. ....................... 382/124; 382/125; 382/126; 382/127
(58) Field of Classification Search ................ 382/115, 382/124, 126, 127, 313, 314, 315, 125; 340/5.52, 340/5.53, 5.82, 5.83, 356; 358/496, 497, 358/486; 250/234

See application file for complete search history.

(56) References Cited

U.S. PATENT DOCUMENTS

| | | | | |
|---|---|---|---|---|
| 4,699,149 A | * | 10/1987 | Rice | 600/475 |
| 6,327,376 B1 | * | 12/2001 | Harkin | 382/124 |
| 6,963,660 B1 | * | 11/2005 | Tsukamura et al. | 382/124 |
| 6,980,669 B1 | * | 12/2005 | Uchida | 382/115 |

FOREIGN PATENT DOCUMENTS

| | | |
|---|---|---|
| JP | 7-21373 | 1/1995 |
| JP | 7-171137 | 7/1995 |
| JP | 10-127609 | 5/1998 |

(Continued)

*Primary Examiner*—Brian Le
(74) *Attorney, Agent, or Firm*—Westerman, Hattori, Daniels & Adrian, LLP.

(57) ABSTRACT

The organism authenticating apparatus 71 of this invention comprises a means that fixes the position of a hand or a finger of a hand, an infrared ray radiating means 97 that radiates infrared rays, an infrared ray image input means 91 that is placed at the opposite side of said hand or said finger of a hand with regard to said infrared ray radiating means, an organism recognizing means that recognizes that the organism is live, a processing means that processes data that are inputted by said infrared ray image input means so that it collates them with image data that are registered in advance and an output means that outputs the result of processing carried out by said processing means. By using this invention, it becomes possible to obtain a clear blood vessel pattern image by a compact size apparatus by using an infrared ray source and by capturing the passed-through infrared ray image of the organism, and it becomes possible by using an organism recognizing means to prevent false authentication.

3 Claims, 17 Drawing Sheets

FOREIGN PATENT DOCUMENTS

| | | |
|---|---|---|
| JP | 11-15948 | 1/1999 |
| JP | 11-102431 | 4/1999 |
| JP | 1-203452 | 7/1999 |
| JP | 11-197135 | 7/1999 |
| JP | 11-203452 | 7/1999 |
| JP | 11-347015 | 12/1999 |
| JP | 2000-5148 | 1/2000 |
| JP | 2002-5148 | 1/2000 |

* cited by examiner

Fig. 15

| 0 | -1 | -1 | -1 | 0 |
|---|----|----|----|---|
| -1 | 0 | 2 | 0 | -1 |
| -1 | 2 | 5 | 2 | -1 |
| -1 | 0 | 2 | 0 | -1 |
| 0 | -1 | -1 | -1 | 0 |

ORGANISM AUTHENTICATING APPARATUS

The invention provides an organism authenticating apparatus, or especially an organism authenticating apparatus that realizes high authentication accuracy by a simple apparatus structure.

BACKGROUND OF THE INVENTION

Several authentication methods using an image of a blood vessel pattern of a human hand have been proposed recently as one way of organism authenticating. In JP, A, H08-508419, for example, an apparatus for authenticating a person by using a vein image of the back of a human hand is presented.

Such conventional organism authenticating methods as exemplified above, however, have several drawbacks; it is difficult to get a clear blood vessel image, the apparatus size cannot be small enough for actual applications, and there is a possibility that a wrong person is authenticated as the principal.

DISCLOSURE OF THE INVENTION

The purpose of the invention is to solve such problems of conventional technologies and to provide an organism authenticating apparatus that enables authenticating an organism at high accuracy using a simple apparatus structure.

In order to attain this purpose, the organism authenticating apparatus of this invention is characterized in that it comprises a means that fixes the position of a hand or a finger of a hand, an infrared ray radiating means that radiates infrared rays, an infrared ray image input means that is placed at the opposite side of said hand or said finger of a hand with regard to said infrared ray radiating means, an organism recognizing means that recognizes that the organism is live, a processing means that processes data that are inputted by said infrared ray image input means so that it collates them with image data that are registered in advance and an output means that outputs the result of processing carried out by said processing means.

By applying this invention, it becomes possible to obtain a clear blood vessel pattern image by a compact size apparatus by using an infrared ray source and by capturing the passed-through infrared ray image of the organism, and it becomes possible by using an organism recognizing means to prevent false authentication.

DESCRIPTION OF DRAWINGS

FIG. 15 is a figure to explain the structure of the spatial filter in the second embodiment example of the invention.

DESCRIPTION OF PREFERRED EMBODIMENT

Preferred embodiment examples of the invention are explained in detail in the following, referring to figures.

THE FIRST PREFERRED EMBODIMENT EXAMPLE

Figure 1:
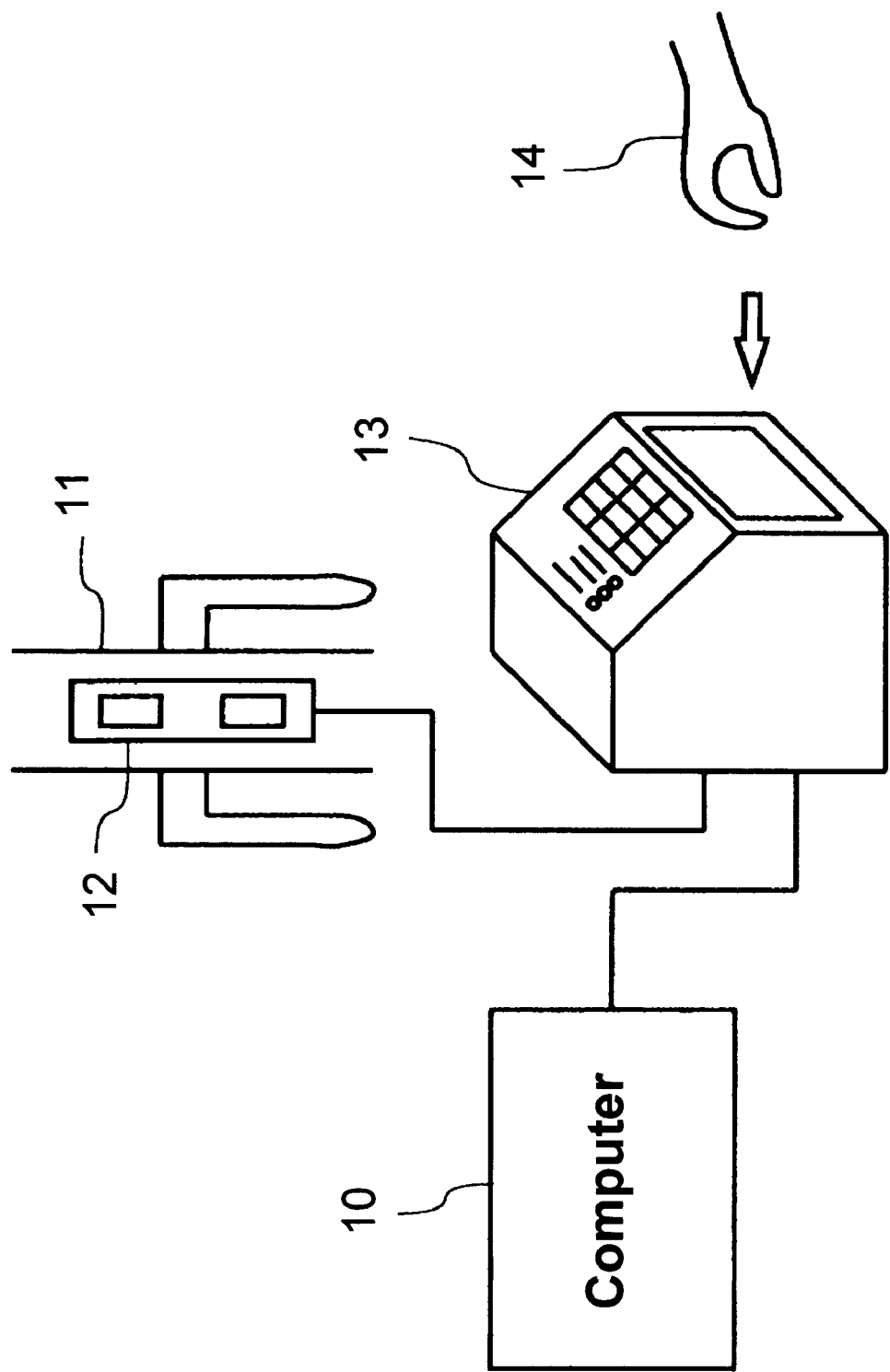
FIG. 1 is a figure to explain the structure of a room entrance management system that uses the organism authenticating apparatus of the invention.

FIG. 1 is a figure to explain the structure of a room entrance management system that uses the organism authenticating apparatus of the invention. In the figure, the organism authenticating apparatus of the invention 13 is connected to the electric lock 12 on a door 11. The door is normally locked by the lock. A person who intends to enter the room first inputs the person's ID number by using the ten-key input board on the front panel of the organism authenticating apparatus 13. The person then puts the person's hand in the aperture of the apparatus and holds the gripping portion within the apparatus.

When the organism authenticating apparatus 13 detects that the hand holds the gripping portion, the apparatus 13 lights infrared ray emitting diodes within the gripping portion, inputs the passed-through infrared ray image of the hand by using a CCD image captor attached above the gripping portion and then collates the inputted image data with image data of permitted persons that are registered in advance. If the person is authenticated by the collation, the electric lock 12 is driven to open. Although it is not indispensable for the invention, the computer 10 is used for recording entrance and exit of persons, storing registered persons' data and executing maintenance and monitoring jobs.

Figure 2:
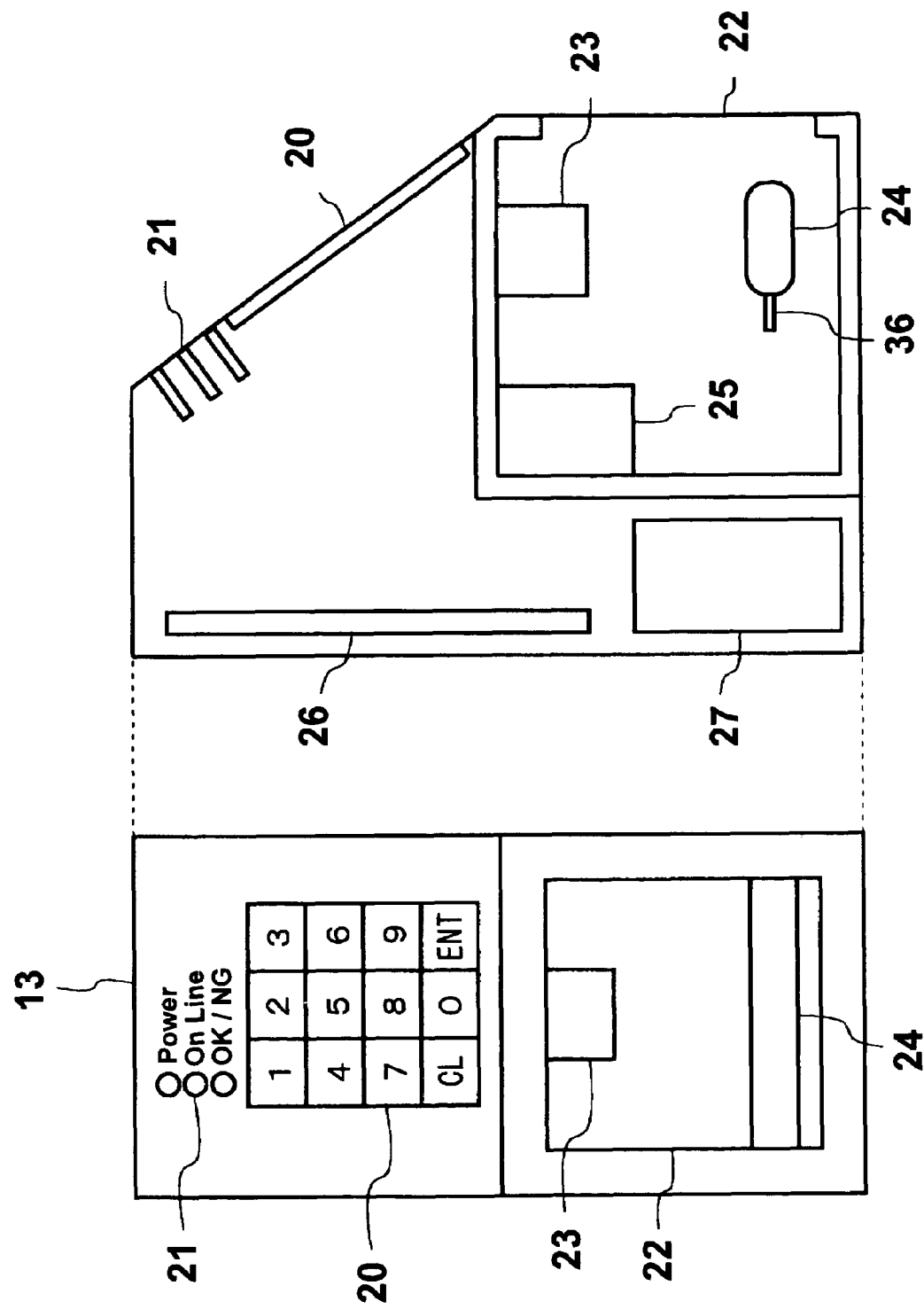
FIG. 2 is a figure to show the structure of the organism authenticating apparatus of the invention by using the front view and the cross-section view from the right side of the apparatus.

FIG. 2 shows the structure of the organism authenticating apparatus of the invention by using the front view and the cross-section view from the right side of the apparatus. A ten-key input board 20 and LED's 21 for status indication are mounted on the front panel at the upper portion of the organism authenticating apparatus 13. An aperture 22 is provided at the lower portion of the organism authenticating apparatus 13. The inside of the aperture 13 is shaped like a box wherein a gripping portion 24 with pins 36 on it is horizontally located at the center of the box.

The image input portion 23, which is actually a CCD image captor, is installed at the inner upper portion of the box, and a sterilizing apparatus 25 that generates ozone for sterilization is installed at the upper end portion of the box. A rotary lid or a curtain may be attached to the apparatus to cover the aperture 22. A printed board 26 on which control circuits that will be explained later are mounted and a power supply unit 27 are also equipped within the organism authenticating apparatus 13.

Figure 3:
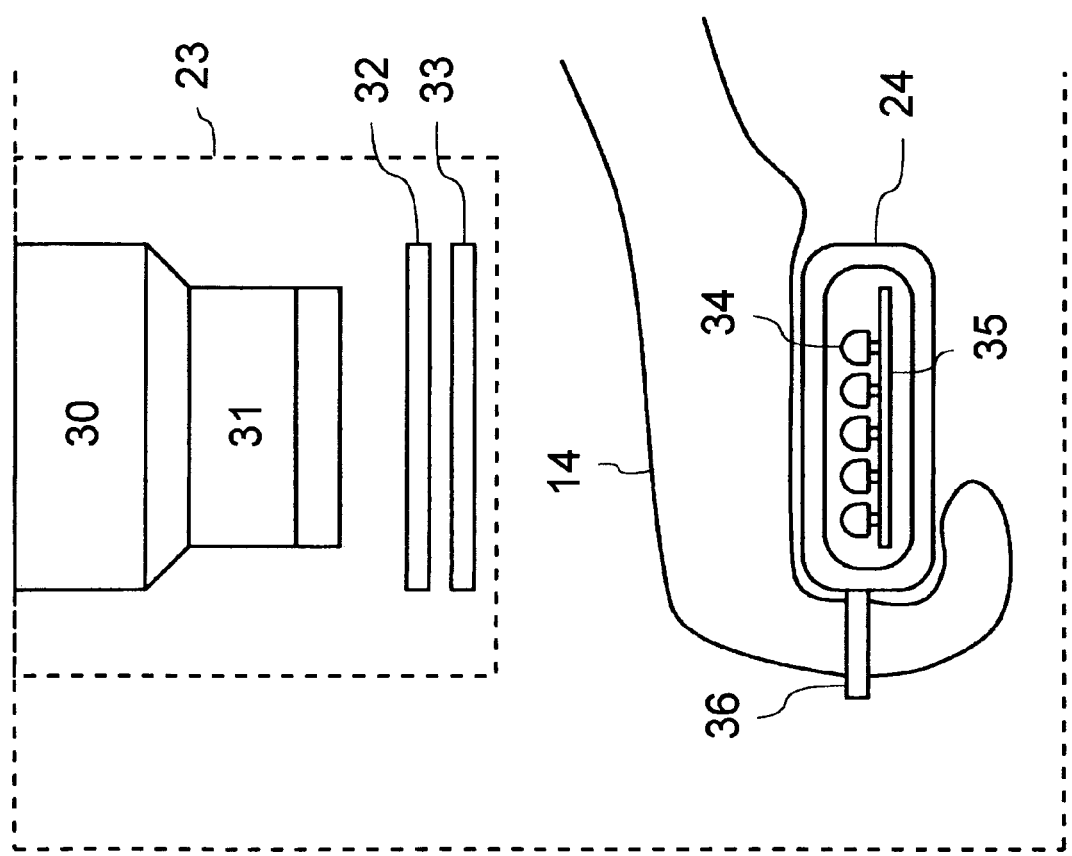
FIG. 3 is a cross-section view to show the structure of the gripping portion 24 and the image input portion 23.
Figure 4:
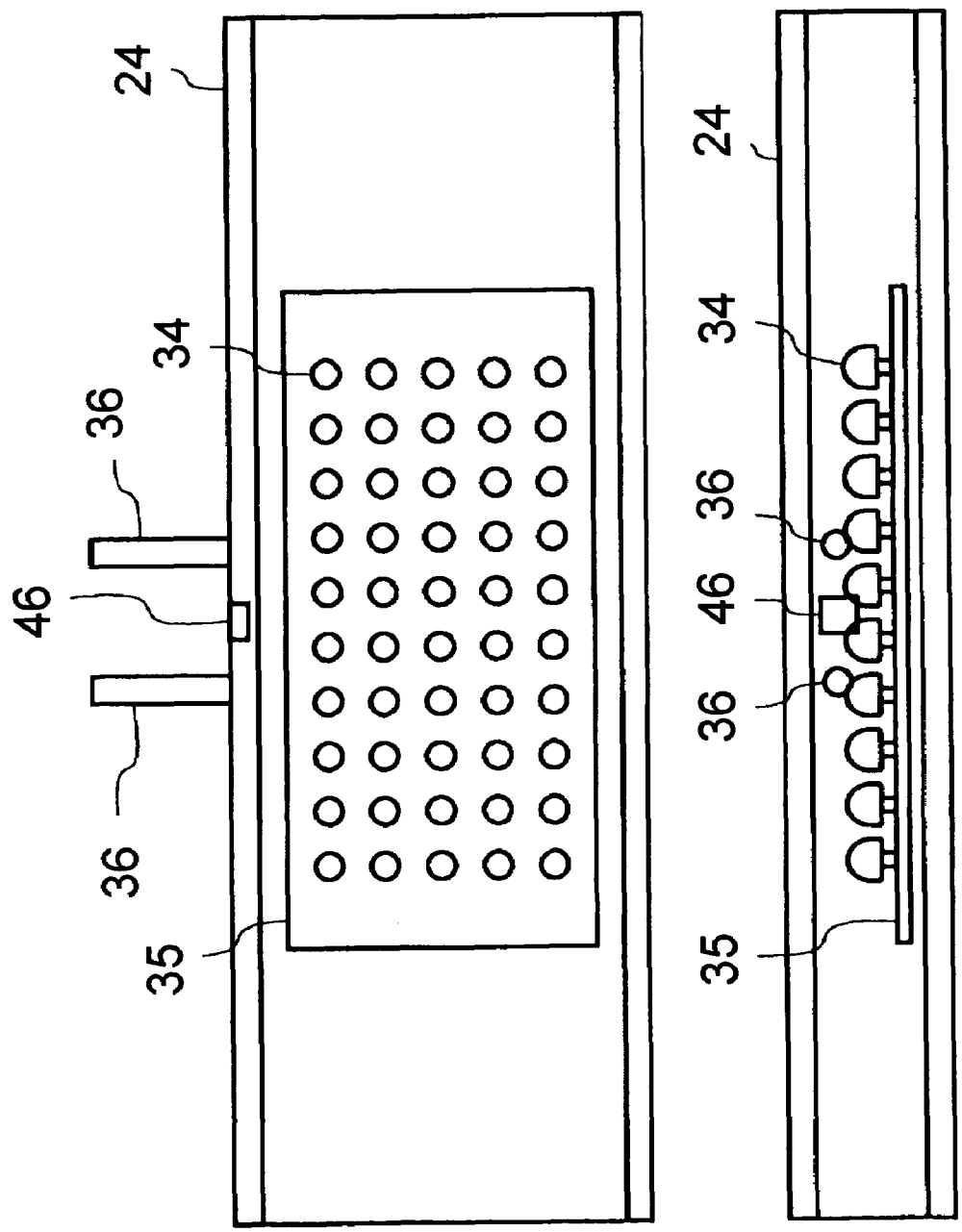
FIG. 4 is a figure to show the structure of the gripping portion 24 by using the front view and the side view.

FIG. 3 is a cross-section view to show the structure of the gripping portion 24 and the image input portion 23. FIG. 4 shows the structure of the gripping portion 24 by using the plane view and the side view. The cross section shape of the gripping portion 24 is a rectangle with round corners as shown in FIG. 3. The gripping portion 24, or at least the upper portion of the gripping portion 24, is made from material that passes through infrared rays such as acryl or vinyl chloride. The gripping portion 24 contains a cavity, and within it the light source board 35 is equipped on which many infrared ray emitting diodes 34 that radiate infrared rays at the wavelength around 850 nm are mounted.

Two metal pins 36 and a thermister 46 for temperature measurement are mounted at the back side of the gripping portion 24. The space between those two pins is set to a size that the middle finger of a hand fits in. Although connecting wires are not drawn in figures, pins 36, the thermister 46 and the light source board 35 are connected to the control board 26.

The image input portion 23 that is installed at the inner upper portion of the organism authenticating apparatus 13 consists of a CCD camera 30, a lens 31 and two optical filters 32 and 33 as shown in FIG. 3. An ordinary CCD camera and lenses that are available on the market can be used as far as they have reasonable sensitivity in the infrared region. The first filter 32 passes only rays with wavelengths longer than 750 nm, for example, and the second filter passes only rays with wavelengths shorter than 900 nm, for example. By using these two filters as a pair, a band pass filter with the pass band between 750 nm and 900 nm can be obtained.

In contrast to conventional methods that can obtain only an image of a vein pattern near the surface of a hand by using the reflected light for taking the image, the organism authentication apparatus of this invention can take a clear image of a blood vessel pattern not only for veins but also for arteries within the hand by using infrared rays passed through the hand for taking the image, as FIG. 3 shows. Bones in the hand do not disturb the blood vessel pattern image, since infrared rays pass through bones.

Figure 5:
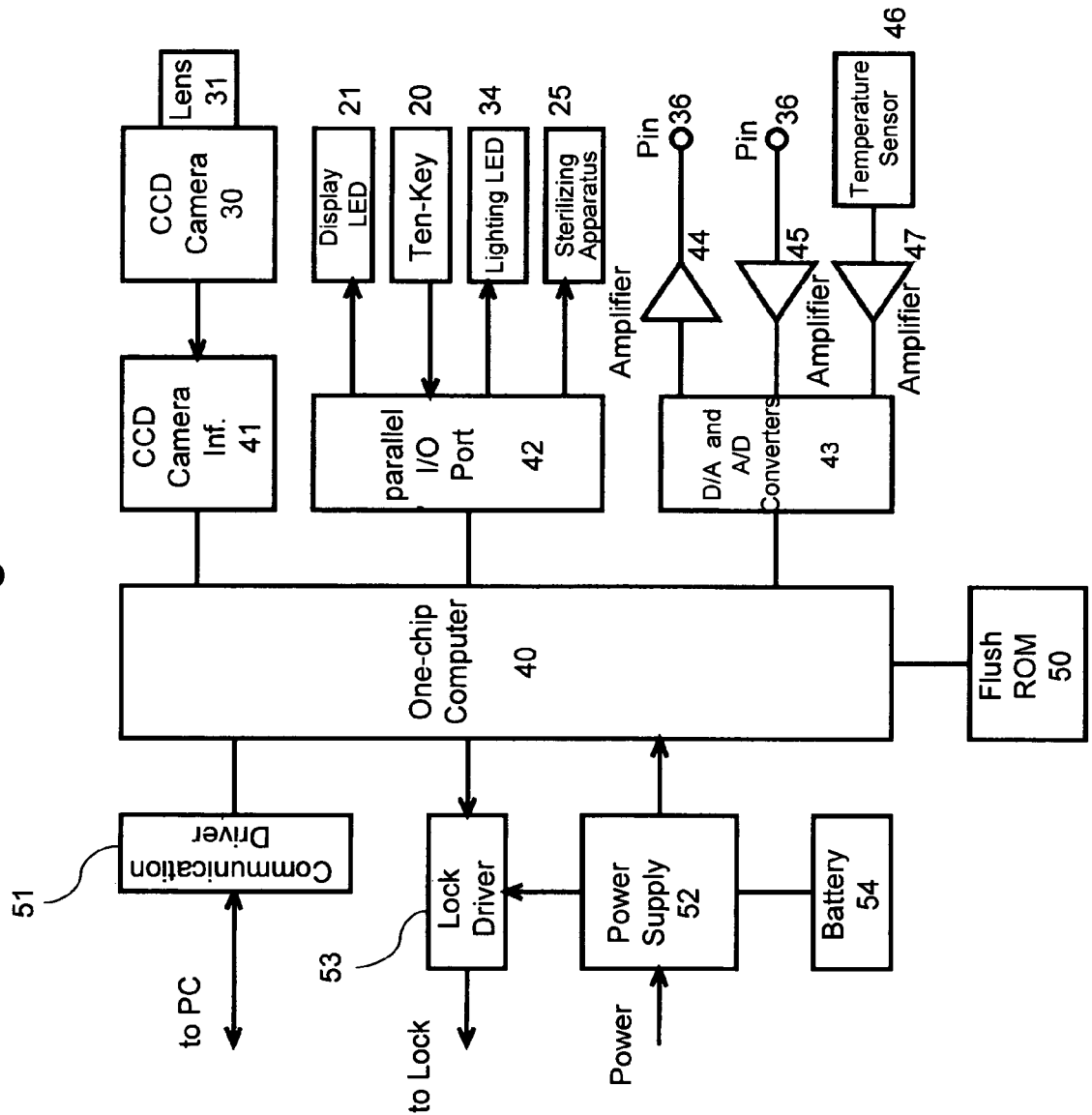
FIG. 5 is a block diagram to show the circuit structure of the organism authenticating apparatus of the invention.

FIG. 5 is a block diagram to show the circuit structure of the organism authenticating apparatus of the invention. The one-chip computer 40 in the figure is a commercially available 16 bit one-chip computer having such circuits as a CPU, a ROM, a RAM, I/O ports, a memory bus, a clock circuit and an interruption circuit. The CCD camera interface circuit 41 takes digital image information (multi-level luminosity data) that is outputted by the CCD camera 30 into the computer 40.

The parallel I/O port 42 takes input data from the ten-key input board 20, and controls turning on and off the LEDs for displaying 21, the LEDs as infrared light sources 34 and the sterilizing apparatus 25. The sterilizing apparatus 25 is driven by a driver circuit that is not shown in the figure. The infrared LEDs for lighting 34 are driven by current that exceeds the luminosity saturation current value at which LED luminosity will not increase any more, in order to assure uniform lighting by reducing luminosity difference among LEDs.

The D/A conversion function of the D/A and A/D converters 43 converts the digital driving signal to the analog driving signal and applies it to the buffer amplifier 44, in order to provide the driving signal to one of the two pins 36. The A/D conversion function of the D/A and A/D converters 43 converts the analog voltage (signal) of the other one of two pins 36 to a digital signal, and also converts the analog output signal of the buffer amplifier 47 that is fed from the temperature sensor (thermister) 46 to a digital signal. Buffer amplifiers 44, 45 and 47 are operational amplifiers (DC amplifiers).

The flush ROM 50 is used mainly for storing registered image data. An arbitral storage device such as an EE PROM, an SRAM, a hard disk or a floppy disk can be also used for this purpose, or the data can be directly read from the computer 10 shown in FIG. 1.

The communication driver 51 provides the line driver function and the line receiver function that conform to RS-232C specifications, for example. The power supply circuit 52 provides the whole organism authenticating apparatus with electric voltages by taking in electric power from the commercial electric source, or from a battery that is equipped in the organism authenticating apparatus in preparation for a power failure. The lock driver 53 outputs a signal to drive the solenoid of the electric lock 12 for opening the lock under the control of the one-chip computer 40.

Figure 7:
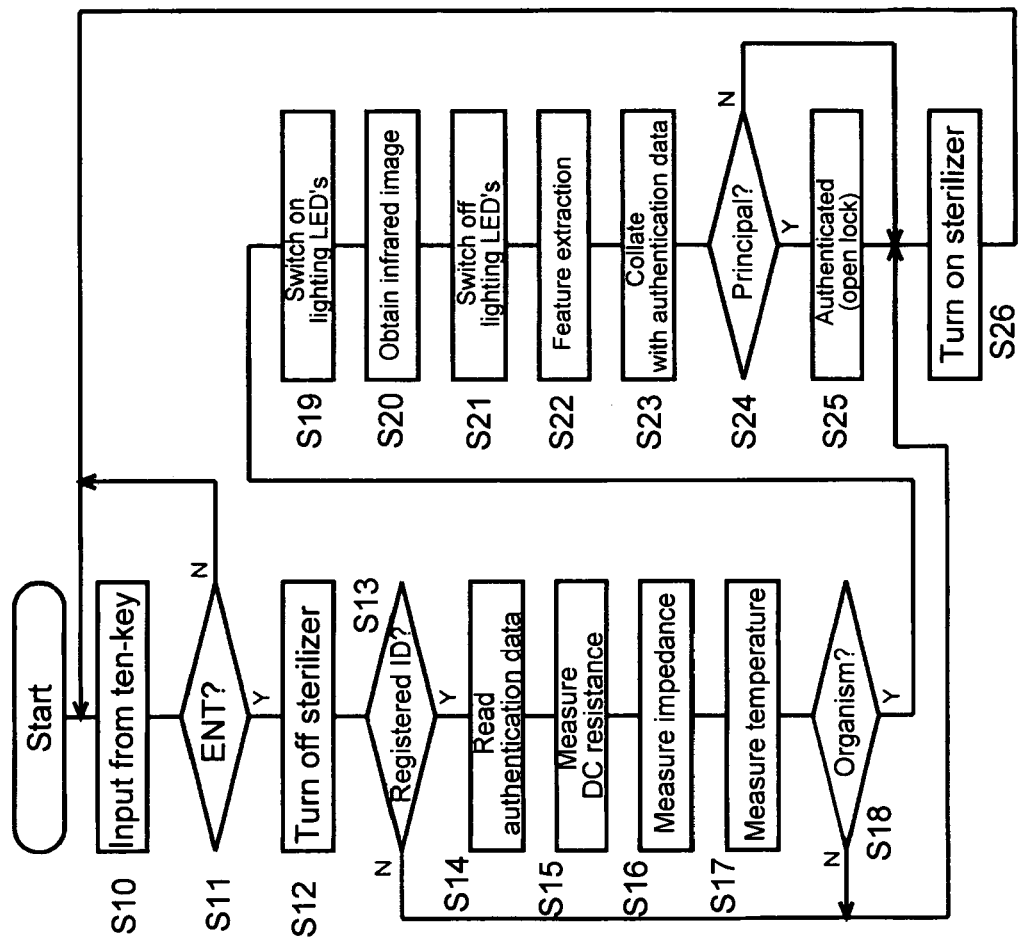
FIG. 7 is a flowchart to show the contents of the control program of the invention.

FIG. 7 is a flowchart to show the contents of the control program of the invention. At the step S10 in the figure, input data is inputted by using the ten-key input board and stored. At the step S11, whether the inputted data matches the data corresponding to the ENT (ENTER) key or not is checked. The process moves to the S12 if the result is "Yes", and goes back to S10 if it is "No".

The sterilizing apparatus is switched off at the step S12. Whether the inputted ID number has been already registered or not is checked at the step S13 by comparing the inputted ID number with the registered ones. The process jumps to S26 if the result is "No", and proceeds to S14 if "Yes". The registered data for collation corresponding to the inputting ID number is read out at the step S14.

At the step S15, a DC voltage with a predetermined value is applied to one of the two pins 36 via the D/A conversion function of the D/A and A/D converters 43 and via the buffer amplifier 44, and then the electric potential at the other one of the two pins 36 is measured via the buffer amplifier 45 and via the A/D conversion function of the D/A and A/D converters 43. Then, whether a human hand is touched to the two pins or not is decided by checking whether the value of the measured electric potential is within a predetermined value range or not. If the measured electric potential does not exceed a predetermined value within a certain predetermined time period, or if the CL (clear) key of the ten-key input board is pushed down, the process goes to the step S26.

At the step S16, the impedance between the two pins 36 is measured. In more detail, an AC voltage with a predetermined amplitude and a predetermined frequency (several tens of KHz, for example) is applied to one of the two pins 36 through the D/A conversion function of the D/A and A/D converters 43 and the buffer amplifier 44, and the voltage waveform at the other one of the two pins 36 is read through the amplifier 45 and the A/D conversion function of the D/A and A/D converters 43. Whether an organism touches to the pins or not is decided by checking whether the amplitude and the phase of the inputted voltage waveform are within a predetermined range or not.

At the step S17, the electric potential that is outputted by the temperature sensor (thermister) 46 is read after A/D conversion, and whether the inserted object is an organism or not is decided by checking whether the measured result is within a predetermined value range or not. At the step S18, whether all of the checking results by steps S15, 16 and 17 indicate that the inserted object is an organism or not. If not, the process jumps to the step S26, and if yes, the step S19 follows.

Infrared LEDs for lighting are lit at the step S19, and then at the step20, the CCD camera 30 is activated to take an infrared ray image through the interface circuit 41. Infrared LEDs for lighting are distinguished at the step S21. Since a large electric current is required to drive infrared LEDs, the electric current is controlled to flow only for a minimum time period necessary for image obtaining.

At the step S22, the inputted image data is processed for edge (contrast) stressing, binary coding and further vectorization, for example, and then feature extraction is carried out by using positions and relationships between end points or branch points of the image. At the step S23, the extracted feature point data is collated to the registered feature point data that is read out at the step S14. Conventional already-known methods for image processing, extracting feature points and collating can be applied to the processes explained above.

At the step S24, whether the result of collation is affirmative or not, that is, whether the person is the principal or not is decided. If the result is "No", the process jumps to the step S26, and if "Yes", then the step S25 follows. At the step S25, the LED for showing that authentication is passed is lit and the electric lock 12 is opened by driving the lock driver 53.

The sterilizing apparatus is switched on at the step S26, and then the process returns to the step S10. At the step S26 also, processed contents such as the ID number, the authentication result and the collated data can be outputted to the computer 10 through the communication driver 51.

Figure 8:
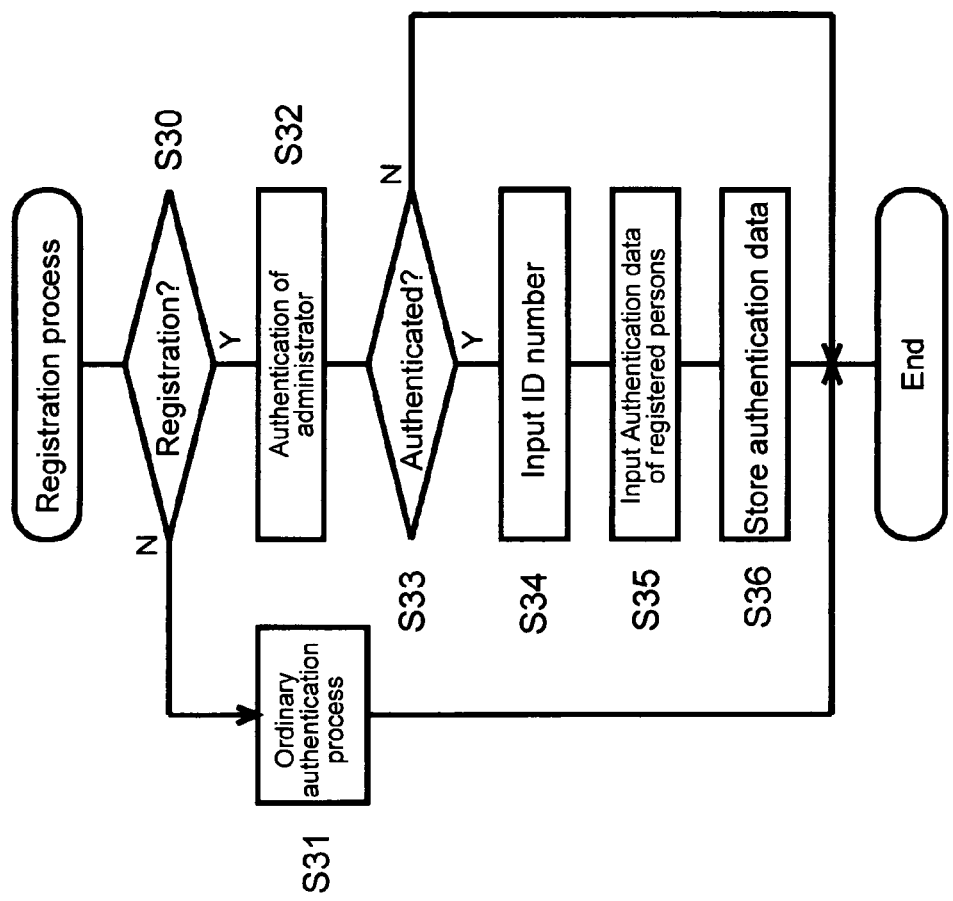
FIG. 8 is a flowchart to show the contents of the registration process.

FIG. 8 is a flowchart to show the contents of the registration process. The flowchart shown in FIG. 7 depicts an example where data for authentication is already registered. In an actual case, however, data for authentication is registered in advance only for one or a few managers who administrate entering/leaving the room, at the initial setting stage of the organism authentication apparatus, for example, and arbitral one of those managers performs on the spot the registration process for other persons who are admitted to enter and to leave the room, as is shown in the following.

At the step S30 in FIG. 8, whether registration should be carried out or not is decided by checking whether a predetermined special ID number is inputted or not. If the result is "No", that is, if the inputted number is not the special ID number, the process goes to the step S31 where the ordinary authentication process from the step S10 to the step S26 in FIG. 7 is carried out. If the result is "Yes", then the step S32 follows.

At the step S32, authentication of the manager is first carried out. This authentication process for the manager is the same as the process from the step S12 to the step S26 in FIG. 7, except that the ID number is determined in advance in this case. Whether the authentication result for the manager is affirmative or not is decided at the step S33. If the manager is authenticated at this step, the process advances to the step S34, while if not, the process is terminated.

At the step S34, a new ID number that is to be registered is inputted by using the ten-key input board. Then, the data for authenticating the new person to be registered is inputted at the step S35. That is, steps S15 to S22 in FIG. 7 are carried out to perform recognizing the organism, obtaining a blood vessel pattern image and extracting features in the image. At the step S36, the obtained data for authenticating the person is memorized and maintained in relation to the person's ID number. Through apparatus configuration and processing steps explained heretofore, it becomes possible to authenticate an organism accurately using a small size apparatus.

Figure 6:
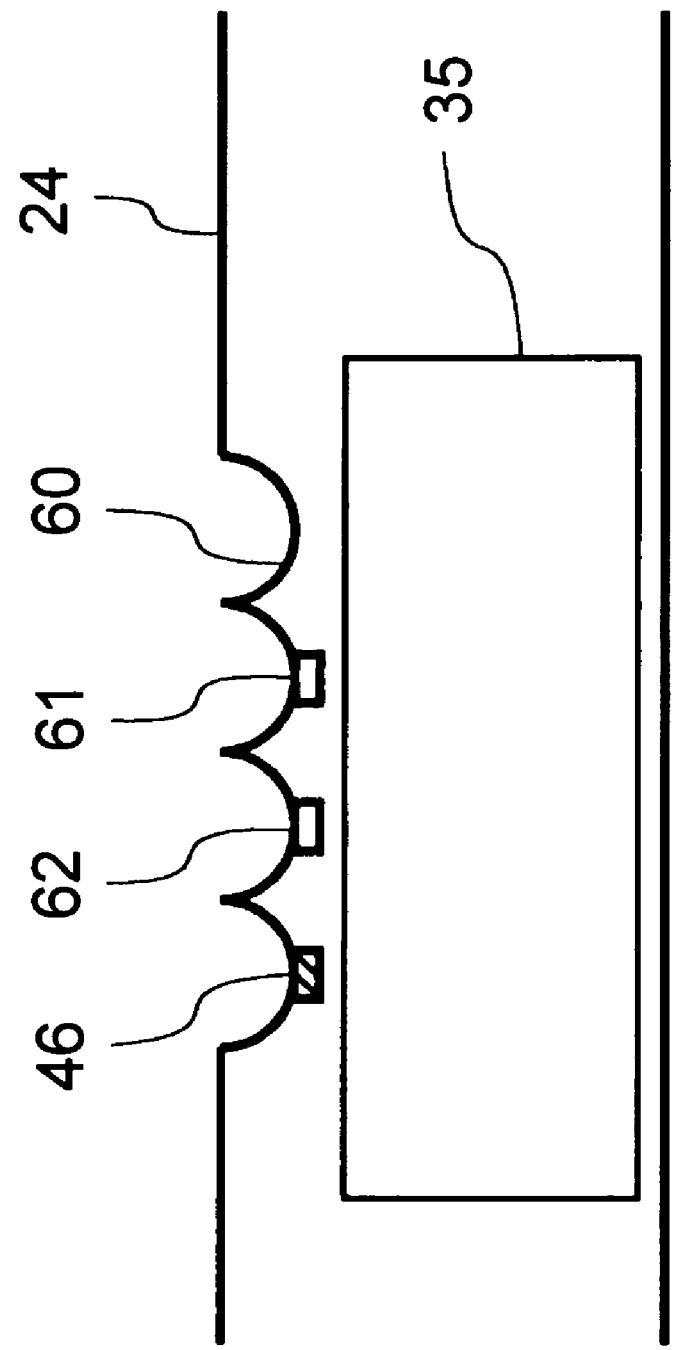
FIG. 6 is a front cross-section view to show the structure of the second embodiment example of the gripping portion 24.

FIG. 6 is a front cross-section view to show the structure of the second embodiment example of the gripping portion 24. In contrast to the first embodiment example of the gripping portion where two pins are used both for fixing a hand to the proper position and for using as electrodes for organism recognition, the second embodiment example of the gripping portion uses hollows that are cut on the gripping portion 24 for fixing the hand, and uses metallic plates, metallic leaves or gilts as electrodes for organism recognition.

As shown in FIG. 6, the infrared ray source board 35 is contained within the second embodiment example of the gripping portion 24. Four dents 60 corresponding to four fingers of the hand excluding the thumb are cut on the surface of the gripping portion 24. Two electrodes 61 and 62, gilts for example, are formed at the bottom of two hollows corresponding to the middle finger and the third finger. A thermister 46 as a temperature sensor is mounted at the bottom of the hollow corresponding to the forefinger. Positions of electrodes 61 and 62 and the temperature sensor 46 can be arbitrarily determined as far as they touch fingers or a hand and unless they hinder the CCD camera for capturing the blood vessel image.

THE SECOND PREFERRED EMBODIMENT EXAMPLE

Figure 9:
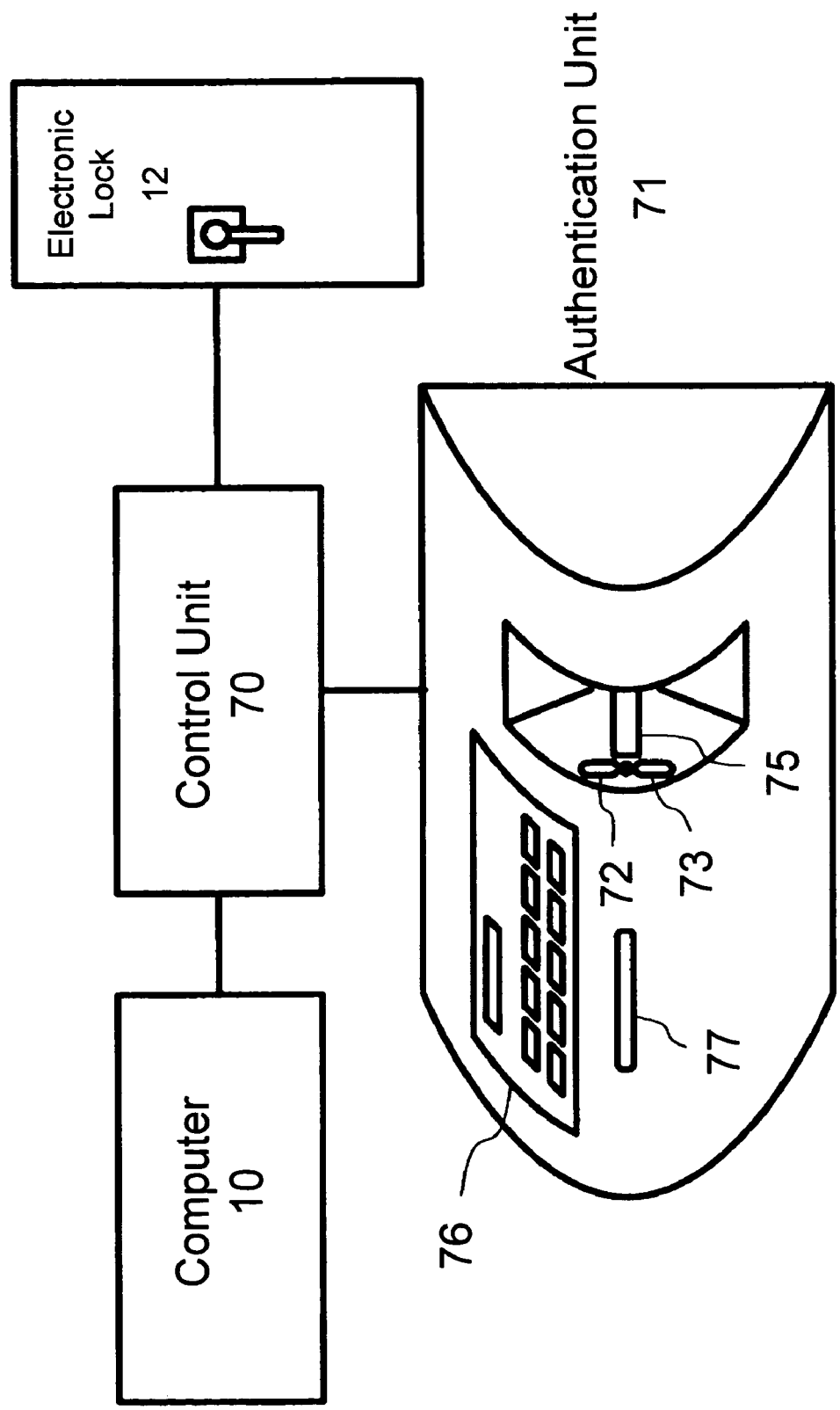
FIG. 9 is a block diagram to show the second embodiment example of the invention.

The second preferred embodiment example of the invention is explained next. FIG. 9 is a block diagram to show the second embodiment example of the invention. Different points from the first preferred embodiment example of the invention are; that the apparatus is divided into the control unit 70 and the authentication unit 71, that a card reader 77 is installed, that recognition of the blood vessel pattern of a finger is carried out and that the recognition mechanism works in the horizontal direction with the finger pressed against the vertical plane.

A control panel 76 with a ten-key input board and an LCD device, a card reader 77 for reading magnetic cards or IC cards and an aperture of the recognition mechanism comprising a CCD camera and infrared LEDs are comprised in the authentication unit 71.

Figure 10:
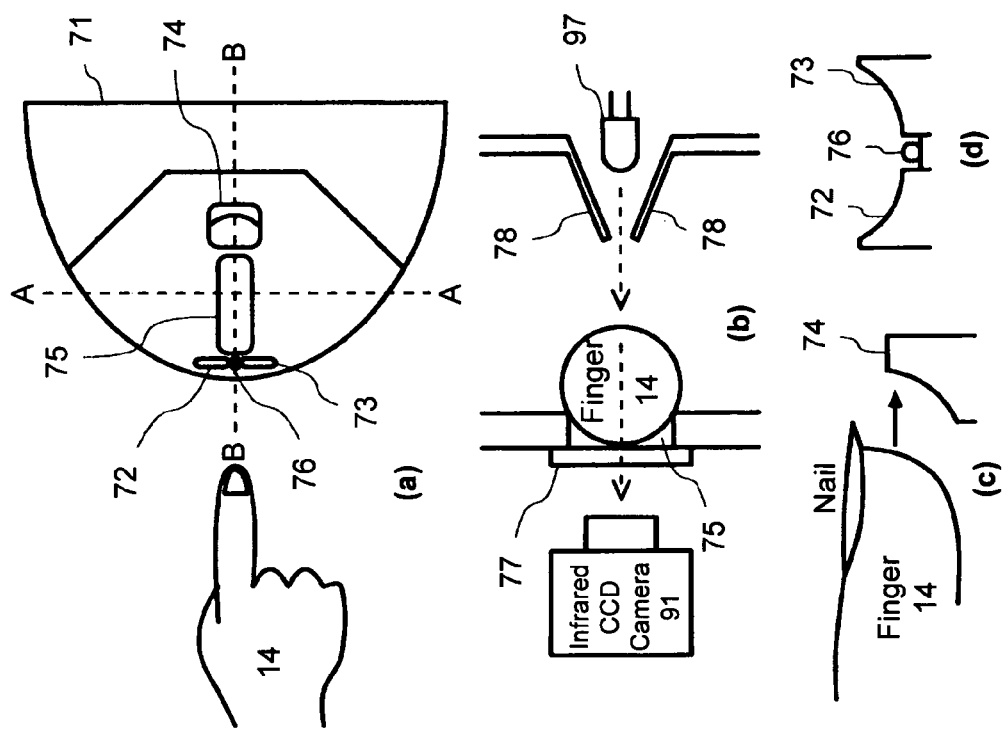
FIG. 10 is a figure to show the structure of the authentication unit in the second embodiment example of the invention.

FIG. 10(*a*) is a cross-sectional view of the authentication unit of the second preferred embodiment example of the organism authentication apparatus of the invention, FIG. 10(*b*) is a cross-sectional view at the line A-A in the figure, FIG. 10(*c*) is a B-B cross-sectional view of the common electrode 74 and FIG. 10(*d*) is a side view of electrodes 72 and 77.

The recognition mechanism is structured to work in the horizontal direction with the finger of a hand 14 pressed against the recognition window 75 that is vertically configured. The recognition window 75 forms a dent that is covered by the finger as shown in FIG. 10(b). The recognition window 75 is sealed by a plate 77 that is made of materials that pass only infrared rays, such as plastics. An infrared CCD camera 91 is positioned at the left side of the recognition window 75. An infrared LED array 97 is placed at the opposite side of the recognition window 75, so that it can radiate infrared rays from the back side of the hand. By using this structure, disturbance in the captured image by wrinkles of the back of the hand can be reduced.

The LED array 97 is an array of ten infrared LEDs placed in line with 5 mm spacing, for example. In front of the LED array 97, two shielding plates 78 that provide with a gap of an appropriate value (3 mm, for example) are attached. Unnecessary infrared rays are cut by these shielding plates 78, so that resolution of the obtained image can be increased.

Although apparatuses shown in FIGS. 9 and 10 are designed for the forefinger of the right hand as an example, the reversed configuration may be used for the left hand, or an apparatus with both structures can be used also.

Two metallic electrodes 72 and 73 that compose a U-shaped finger guide as a whole and a thermister 76 that is placed between the two electrodes are positioned in front of the recognition window 75. These two electrodes 72 and 73 and the thermister 76 are designed to touch the root of the ball side of the forefinger. A common metallic electrode 74 having a dent in the middle portion of it is equipped deep inside of the recognition window 75 as shown in FIG. 10(c). The common electrode 74 is used also as a finger guide and a finger stopper, and is designed to rise lower than the position of the nail of the finger.

By structuring the recognition mechanism to work in the horizontal direction with the finger of a hand pressed against the recognition window to cover the aperture, unnecessary infrared rays from outside can hardly enter the window, and dusts or other foreign materials can hardly stick to the window.

Figure 11:
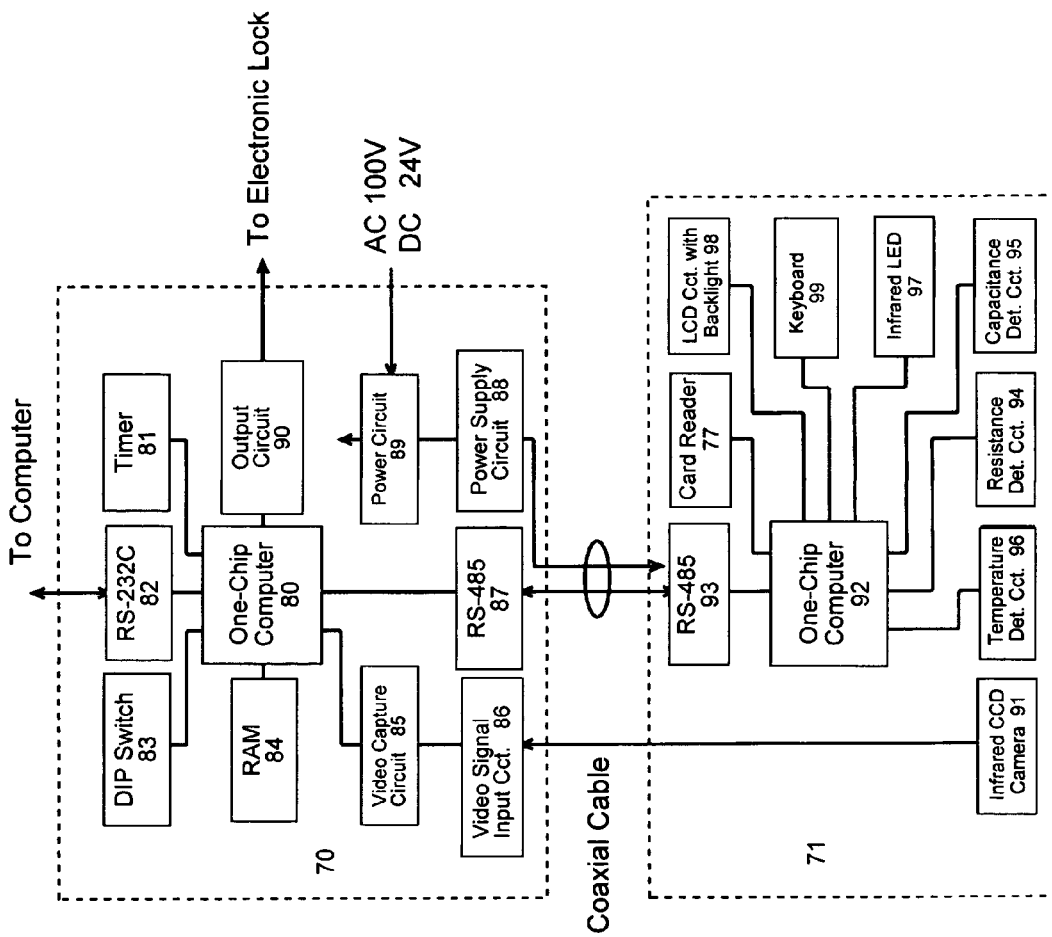
FIG. 11 is a block diagram to show the circuit structure for each unit in the second embodiment example of the invention.

FIG. 11 is a block diagram to show the circuit structure for each unit in the second embodiment example of the invention. An already-known one-chip computer 80 having a CPU, a ROM, a RAM, I/O ports and so on is installed in the control unit 70 in the figure. To this one-chip computer 80, an RS-232C interface circuit 82 that is used for connecting the one-chip computer 80 to another computer 10, a DIP switch 83 that is used for setting the ID and the operation mode of the organism authenticating apparatus of the invention, a timer 81, an output circuit 90 that outputs control signals for the electric lock 12 and others, a RAM 84 that stores registration information, a video capture circuit 85 that captures one frame of a video image signal through A/D conversion by video signal input circuit 80 and an RS-485 interface circuit 87 that communicates with the authentication unit 71 are connected. The computer 80 executes the registration process and the authentication process that will be explained in the following. The power supply circuit 88 provides the authentication unit with electric power.

Another already-known one-chip computer 92 having a CPU, a ROM, a RAM, analog and digital I/O ports and others is installed in the authentication unit 71 in the figure. To this one-chip computer 92, an RS-485 interface circuit 93 that is used for communicating with the other one-chip computer 80 in the control unit, a card reader 77 for magnetic cards or for IC cards, an LCD circuit 98 with a back light and a key input board 99 that are the components of the front panel, infrared LEDs 97, a temperature detection circuit 96, a resistance detection circuit 94 and a capacity detection circuit 95 are connected. The computer 92 executes various kinds of measurement processing and processing related to the panel and the card reader, under the control of the other one-chip computer 80. An already-known infrared CCD camera 91 is connected to the video input circuit 86 of the control unit 70 via a coaxial cable.

Figure 12:
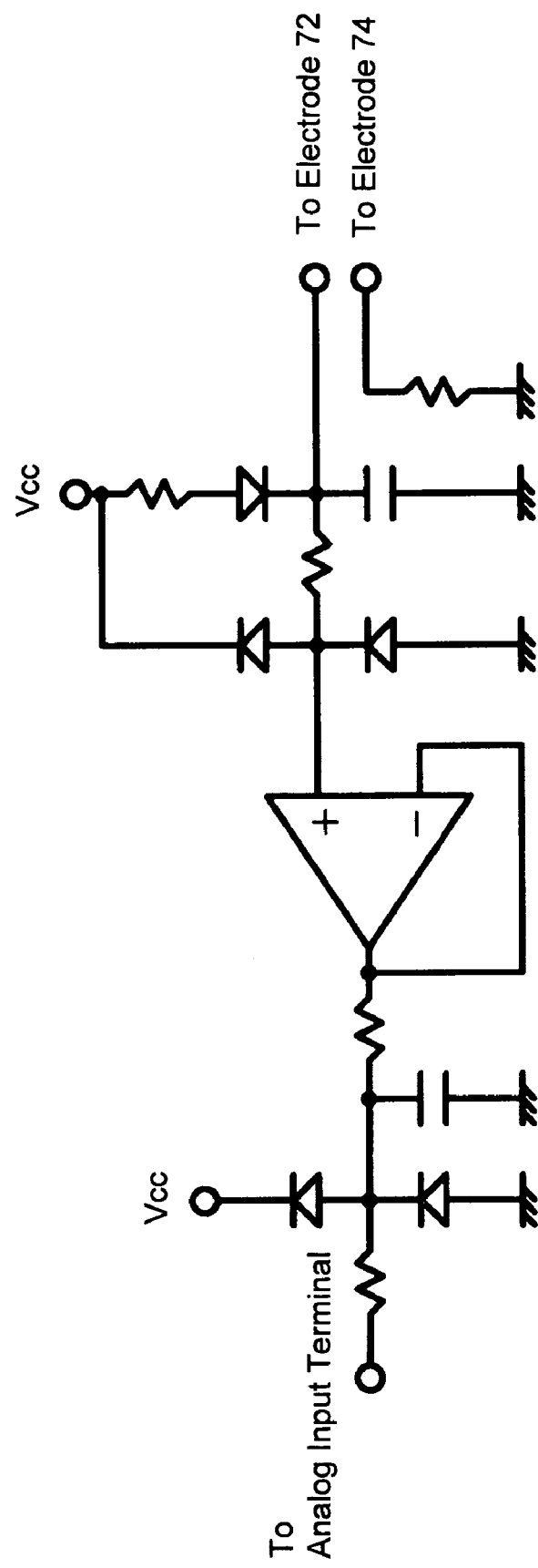
FIG. 12 a block diagram to show the structure of the resistance detection circuit in the second embodiment example of the invention.

FIG. 12 is a block diagram to show the structure of the resistance detection circuit 94 in the second embodiment example of the invention. The resistance detection circuit 94 provides an electric voltage to the electrode 72 through a resister, and measures the voltage between the electrode 72 and the common electrode 74 that varies according to the resistance of a person's finger when the finger is touched to the electrode 72 and the common electrode 74. The measured voltage at the electrode 72 is sent to the analog input terminal of the one-chip computer 92 (the input terminal of an A/D converter contained in the one-chip computer) through a buffer amplifier.

Figure 13:
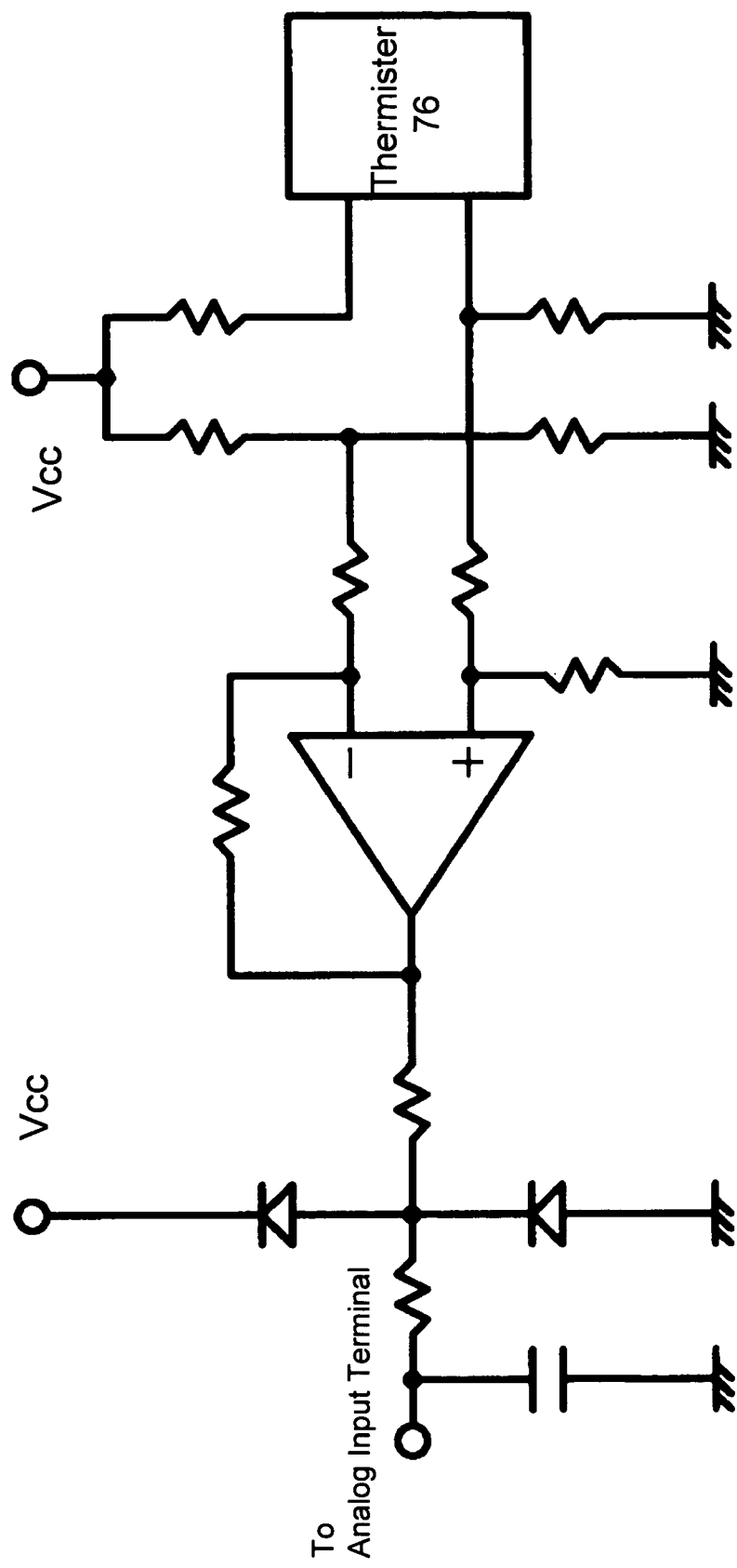
FIG. 13 is a block diagram to show the structure of the temperature detection circuit in the second embodiment example of the invention.

FIG. 13 is a block diagram to show the structure of the temperature detection circuit 96 in the second embodiment example of the invention. The output voltage of the resistor bridge circuit containing the thermister 76 that is a temperature sensitive element as one branch of the bridge is sent to the analog input terminal of the once-chip computer 92 (the input terminal of an A/D converter contained in the one-chip computer) through a differential amplifier using an operational amplifier.

Figure 14:
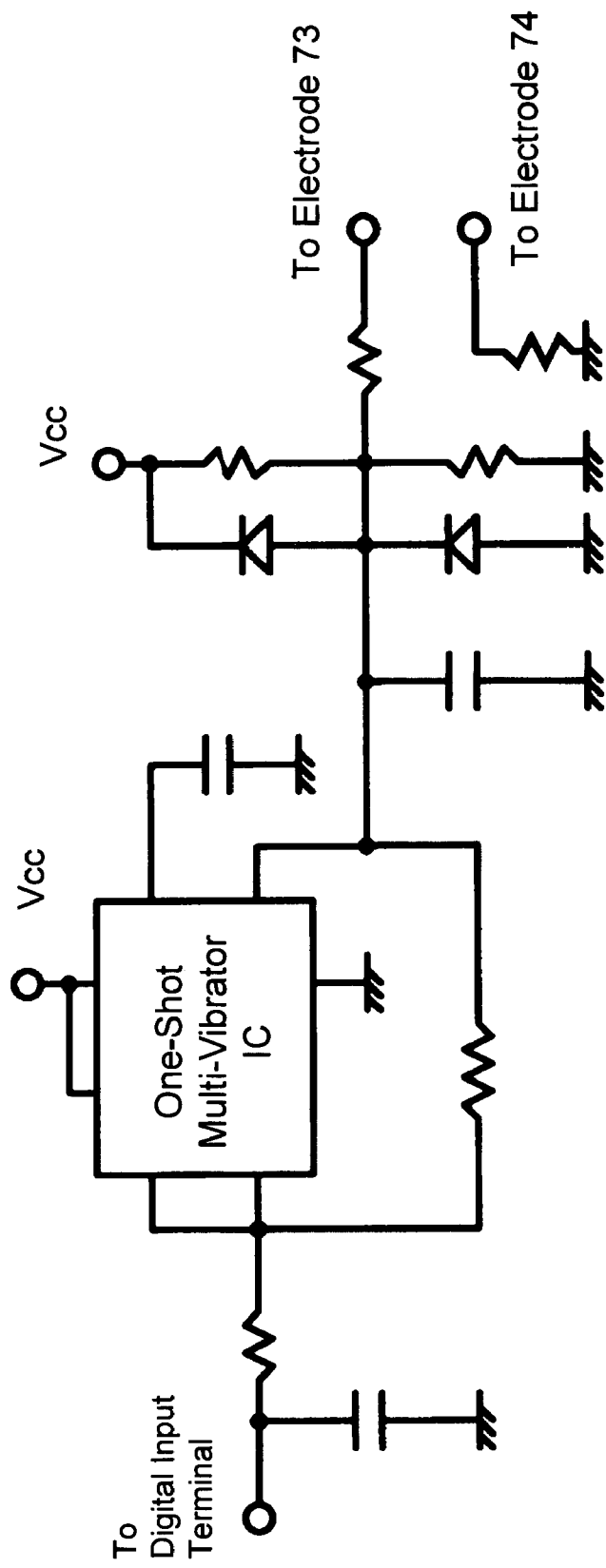
FIG. 14 is a circuit diagram to show the structure of the capacity detection circuit in the second embodiment example of the invention.

FIG. 14 is a circuit diagram to show the structure of the capacity detection circuit 95 in the second embodiment example of the invention. The capacity detection circuit 95 consists mainly of an oscillation circuit that uses an already-known one-shot multi-vibrator IC. The connection point of the resistor and the capacitor that determine oscillation frequency is connected to the electrode 73. When a finger of a person touches the electrode 73 and the common electrode 74, the oscillation frequency varies according to the capacitance (and the resistance) of the finger. The oscillation signal with the rectangular waveform is sent to the digital input terminal of the one-chip computer 92, and the period (frequency) of the rectangular wave is calculated by a program in the computer.

Figure 17:
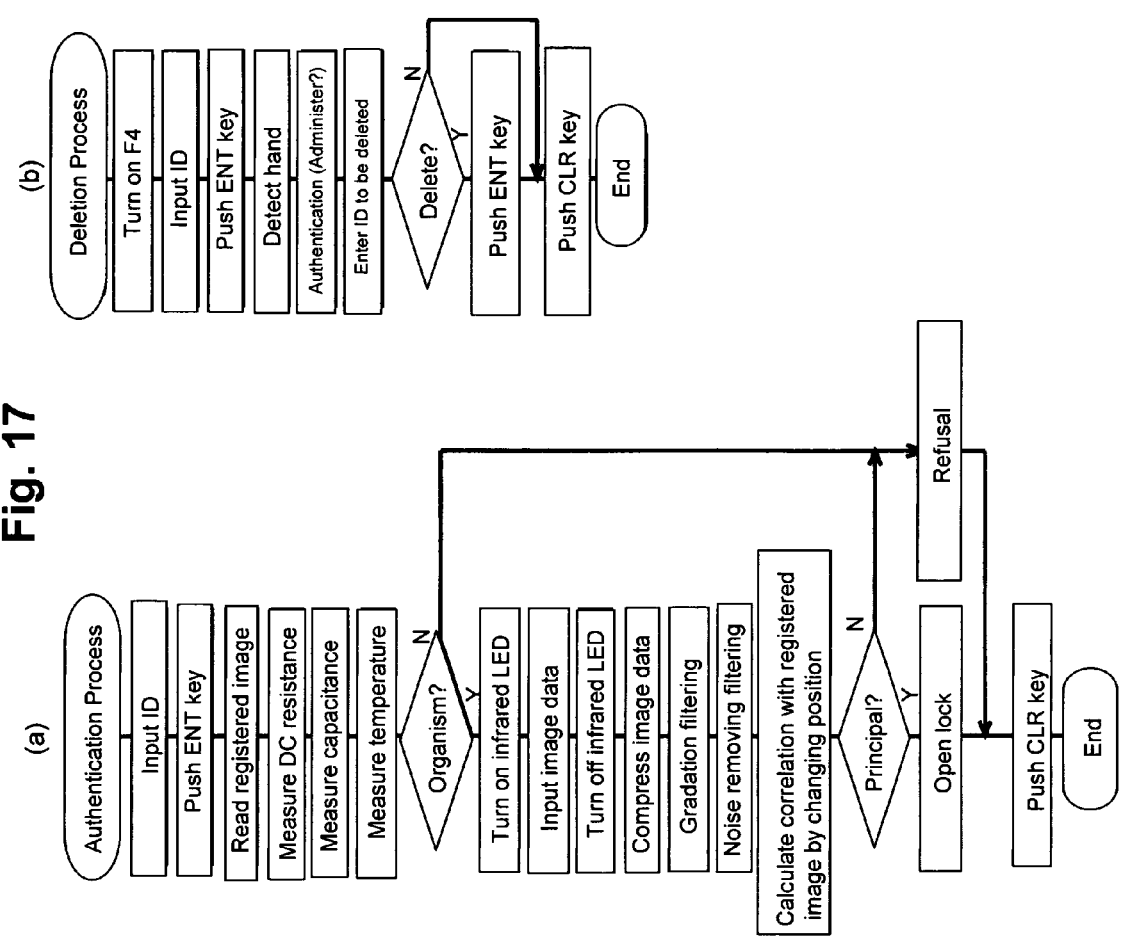
FIG. 17 shows flowcharts to show the contents of the authentication process and the deletion process in the second embodiment example of the invention.

FIG. 17 shows flowcharts to explain the contents of the authentication process and the deletion process in the second embodiment example of the invention. FIG. 17(a) shows the flowchart of the authentication process. A person to be authenticated first inputs the person's ID from the panel and pushes the ENT key. The computer 80 reads the registered image, measures the DC resistance, the capacitance and the temperature and then determines whether the measured object is an organism or not by checking whether these measured values are within a predetermined range, respectively, or not. When it is determined that the object is an organism, the infrared LEDs for lighting 97 is driven by a current with the value at which LED luminosity saturates. Then the computer 80 takes in the infrared ray image data through the CCD camera 91, and turns off the infrared LEDs.

Figure 15:
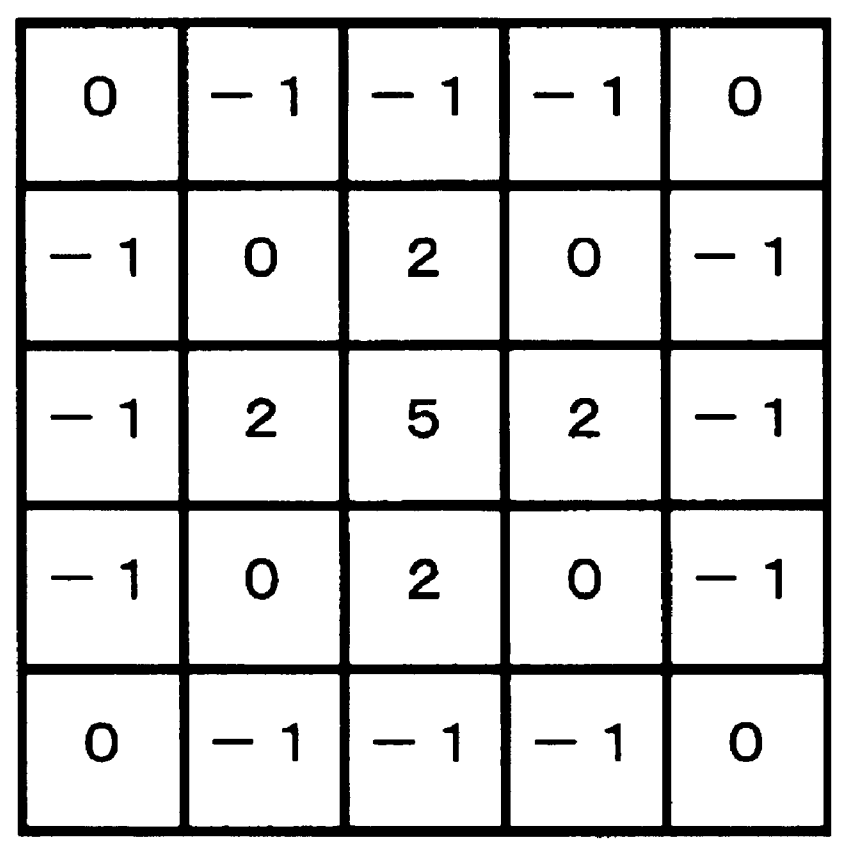

Next, the computer compresses the image data obtained (from 64 KB to 1 KB, for example) and executes gradation emphasizing filtering. FIG. 15 is a figure to explain the structure of the kernel pattern (weighting functions) of the gradation emphasizing filter in the second embodiment example of the invention. The filtering process is such that differential filter coefficients shown in FIG. 15 is multiplied to each of 5×5=25 gradation values around the noticed pixel of the image, and the original noticed pixel value is replaced by the new value that is obtained by adding the result of the multiplication to the original noticed pixel value. Local gradation emphasizing becomes possible by this process.

Next the computer 80 removes trivial noises through noise removing filtering process, and then calculates the value of correlation between the obtained image and the registered image, in order to decide whether the person is the principal or not. In this process, a several number of correlation values are calculated by shifting the position of one of the two images, and the maximum value among the calculated values is adopted as the resultant correlation value. By this process, correct recognition becomes still possible even if the positions of the two images are mutually slipped out, by 2 mm, for example. If the person is recognized as the principal, the lock is opened, and if not, a refusing action such as displaying an "NG" note is taken.

Figure 16:
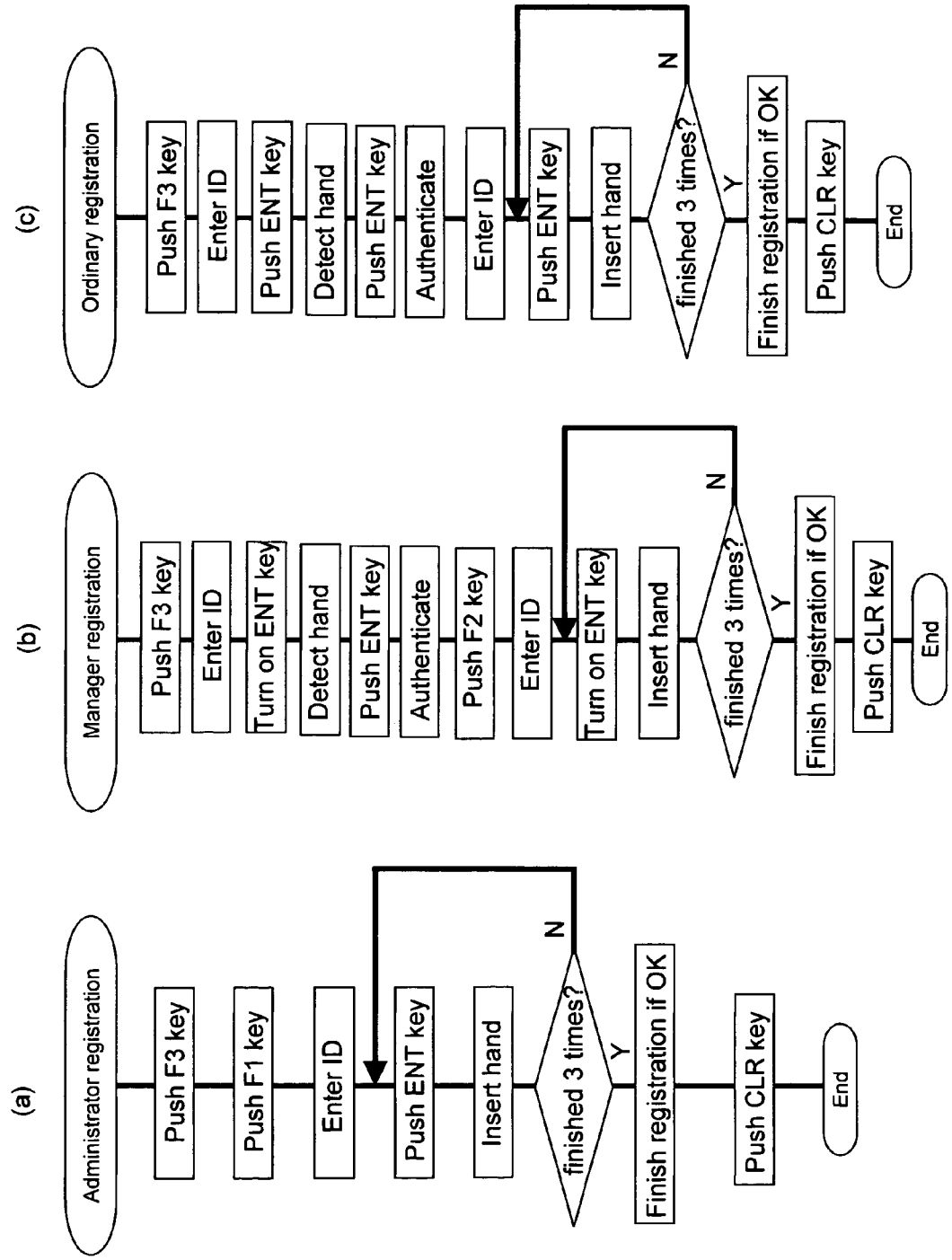
FIG. 16 shows flowcharts to show the contents of the registration processes in the second embodiment example of the invention.

FIG. 16 shows flowcharts to explain the contents of registration processes in the second embodiment example of the invention. FIG. 16(*a*) is a flowchart of the registration process for the administrator (only one manager that has all rights of managing the authentication system). This process is carried out when there are no registered data in the system and the function key F3 of the key board is pushed, for example. The administrator pushes the F3 key, pushes the F1 key, and then repeats three times inputting ID and inserting the administrator's hand (or finger) into the apparatus. The computer 80 calculates correlation values between the inputted data, and if those values exceed a predetermined threshold value, then the computer decides that the data is correct and stores the first inputted and processed image data as the image data of the administrator.

FIG. 16(*b*) is a flowchart of the registration process for a few number of managers who have limited rights of managing the authentication system. The administrator registers managers. In the manager registration process, the administrator first pushes the F3 key, inputs the administrator's ID, pushes the ENT key and makes the apparatus to authenticate the administrator's hand (or finger). Then the manager to be registered pushes the F2 key and inputs the manager's ID, and then repeats three times pushing the ENT key and inserting the manager's hand (or finger) into the apparatus. The computer 80 calculates correlation values between the inputted data, and if those values exceed a predetermined threshold value, then the computer decides that the data is correct and stores the first inputted and processed image data as the image data of the manager.

FIG. 16(*c*) is a flowchart of the registration process for ordinary persons who have no rights of managing the authentication system. Ordinary persons are registered by the administrator or one of managers. In the registration process, the administrator or one of managers first pushes the F3 key, inputs the ID of the administrator's or the manager's, pushes the ENT key and makes the apparatus to authenticate the hand (or finger) of the administrator's or the manager's. Then the ordinary person to be registered inputs the person's ID, and then repeats three times pushing the ENT key and inserting the person's hand (or finger) into the apparatus. The computer 80 calculates correlation values between the inputted data, and if those values exceed a predetermined threshold value, then the computer decides that the data is correct and stores the first inputted and processed image data as the image data of the person.

FIG. 17(*b*) shows the flowchart to explain the contents of the deletion process in the second embodiment example of the invention. Deletion of registered data is allowed only to limited persons having special right, to the administrator, for example. In the deletion process, the administrator, for example, first pushes the F4 key, inputs the ID of the administrator's, makes the apparatus to authenticate the hand (or finger) of the administrator's and then inputs the ID to be deleted. After checking that the ID is correct on the screen displayed, the administrator pushes the ENT key if the deletion should be done. If not, the administrator pushes the CLR key to chancel deletion.

Although several embodiment examples have been shown in the explanation heretofore, other embodiment variations of the invention are possible. Blood vessel pattern image data is used for authentication in examples explained, but other authentication data such as fingerprints, voiceprints, handwritings, blood vessel patterns in the retina or iris patterns may be used in parallel for authentication or for identifying the organism.

ID numbers are inputted by using a ten-key input board in embodiment examples. But in addition to the ten-key input board, a card reader may be equipped for reading ID numbers from ID cards. Not only magnetic cards but also any of other already-known recording media can be used as a recording means for ID numbers. Otherwise, it is possible to get ID numbers through wireless connection, by installing a wireless LAN interface such as the Bluetooth interface in the organism authenticating apparatus.

Furthermore, in the second embodiment example of the invention, it is possible to use an IC card as an information recording medium in which the registered image data is stored, and to collate the registered image data read from the IC card with the image data inputted from the CCD camera for authentication. By doing this, it becomes unnecessary to store the registered image data within the authenticating apparatus.

Measurement of DC resistance, AC impedance or temperature is exemplified as a method for recognizing an organism in the embodiment examples, but in order to recognize an organism further securely, it is possible to detect the flow (movement) of blood (red blood corpuscles) through continuously capturing the enlarged blood vessel image of a hand by using another CCD camera with a close-up lens, or by adding an exchanging mechanism for the lens 31.

Methods of capturing the blood vessel pattern image by using pass-through infrared rays are explained heretofore in the embodiment examples of the invention, but it is possible to get the blood vessel image to a certain extent by using reflected rays.

Although the application to a room entrance management system is exemplified in embodiment examples of the invention, the organism authenticating apparatus of this invention can be combined with or contained in any other systems that require authentication of an individual.

FEASIBILITY OF INDUSTRIAL APPLICATIONS

By applying this invention, it becomes possible to obtain a clear blood vessel pattern image by a compact size apparatus by using an infrared ray source and by capturing the passed-through infrared ray image of the organism, and it becomes possible by using an organism recognizing means to prevent false authentication.

What is claimed is:

1. An organism authenticating apparatus for recognizing a blood vessel pattern of a finger of a hand by using infrared rays passed through the finger, working in a horizontal direction with the finger pressed against a vertical plane of a U-shaped finger guide composed in a gap of the authentication apparatus, and comprising:

a positioner to fix a position of the finger;

an infrared ray radiator to radiate infrared rays;

an infrared ray image input to input an image of a blood vessel pattern of the finger, said infrared ray image input being placed at an opposite side of said finger with regard to said infrared ray radiator;

an organism recognizer to recognize that the organism is live;

a processor that processes data that are inputted by said infrared ray image input so that it collates inputted data with image data that are registered in advance; and an output to output the result of processing carried out by said processor, wherein said infrared ray radiator and said infrared ray image input are structured so that a line connecting said infrared ray radiator and said infrared ray image input is horizontally flat and the finger is placed between the input and the radiator, wherein said organism recognizer measures at least one of a temperature, a resistance, or an impedance at a specified frequency of the finger to be recognized in order to recognize the organism by using electrodes or a temperature sensitive element that are attached to said positioner that fixes the position of the finger of the hand, wherein said processor controls commencement of operation of said infrared ray radiator and said infrared ray image input according to the measurement result measured by said organism recognizer, and wherein said infrared ray radiator comprises a plural number of infrared LEDs that are placed in line and are driven by a current at a saturated level such that a luminosity of the LEDs is maximum, and a shielding means that is provided with a predetermined gap width between a camera and the finger to be recognized in order to cut unnecessary rays except infrared rays.

2. The organism authenticating apparatus claimed in claim 1 wherein said organism authenticating apparatus contains a reader that reads registered image data that is stored in an information recording medium; and said processor collates image data that are inputted by said infrared ray image input and processed by said processor with image data that are read by said reader.

3. The organism authenticating apparatus claimed in claim 1, wherein said organism authenticating apparatus contains a reader that reads registered image data that is stored in an information recording medium; and wherein said processor collates image data that are inputted by said infrared ray image input and that are processed by said processor to image data that are read by said reading means.

* * * * *